(12) United States Patent
Kawasaki et al.

(10) Patent No.: US 8,183,408 B2
(45) Date of Patent: May 22, 2012

(54) PROCESS FOR PRODUCTION OF N-CARBAMOYL-TERT-LEUCINE

(75) Inventors: Hiroaki Kawasaki, Takasago (JP); Katsuji Maehara, Takasago (JP); Tadashi Moroshima, Takasago (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 12/734,661

(22) PCT Filed: Nov. 7, 2008

(86) PCT No.: PCT/JP2008/070300
§ 371 (c)(1),
(2), (4) Date: May 14, 2010

(87) PCT Pub. No.: WO2009/063804
PCT Pub. Date: May 22, 2009

(65) Prior Publication Data
US 2010/0256416 A1     Oct. 7, 2010

(30) Foreign Application Priority Data
Nov. 16, 2007   (JP) ................................ 2007-298435

(51) Int. Cl.
C07C 273/18     (2006.01)
(52) U.S. Cl. ..................................................... 562/560
(58) Field of Classification Search .................. None
See application file for complete search history.

(56) References Cited

U.S. PATENT DOCUMENTS

| 4,645,678 A | 2/1987 | Nofre et al. |
| 6,180,374 B1 | 1/2001 | Turner et al. |
| 7,326,795 B2 | 2/2008 | Sudhakar et al. |

FOREIGN PATENT DOCUMENTS

| EP | 0 495 218 | 12/1991 |
| EP | 0 844 236 | 5/1998 |
| JP | 59-73559 | 4/1984 |
| JP | 60-155968 | 8/1985 |
| JP | 9-504304 | 4/1997 |
| JP | 10-72419 | 3/1998 |
| JP | 2007-332050 A | * 6/2006 |
| JP | 2006-528133 | 12/2006 |
| JP | 2007-332050 | 12/2007 |
| WO | 95/12573 | 5/1995 |
| WO | 2004/113294 | 12/2004 |
| WO | 2007/018941 | 2/2007 |
| WO | 2008/064066 | 5/2008 |

OTHER PUBLICATIONS

Stark, Biochemistry, Reactions of Cyanate with Functional Groups of Proteins III. Reactions with Amino and Carboxyl Groups., 1965, 4(6), pp. 1030-1036.*
International Search Report issued Dec. 2, 2008 in International (PCT) Application No. PCT/JP2008/070300.
Jikken Kagaku Koza, "The course of Chemical Experiment", Maruzen Co. Ltd, 5$^{th}$ edition, vol. 14, p. 429 and its English translation, 2005.
Viret, J. et al., Practical Synthesis of Optically Active α-Hydrazino Acids from α-Amino Acids, Tetrahedron, vol. 43, No. 5 (1987), pp. 891-894.
Japanese Submission of Information by Third Parties (with English translation) dated Jan. 24, 2012 in corresponding Japanese Application No. 2009-541113.
Extended European Search Report issued Feb. 8, 2012 in corresponding European Application No. 08848907.5.
George Barger et al., "The Amino-Acid Methionine: Constitution and Synthesis", The Biochemical Journal, 1928, vol. XXII, No. 6, pp. 1417-1426.
Encyclopedia of Chemical Technology, 1981, pp. 789-794.
Naobumi Oi et al., "Enantiomer Separation by HPLC with Some Urea Derivatives of L-Valine as Novel Chiral Stationary Phases", Journal of Liquid Chromatography, 1986, vol. 9, No. 2 and 3, pp. 511-517.

* cited by examiner

Primary Examiner — Paul A Zucker
(74) Attorney, Agent, or Firm — Wenderoth, Lind & Ponack, L.L.P.

(57) ABSTRACT

The present invention relates to a process for producing an N-carbamoyl-tert-leucine, characterized in mixing tert-leucine with an isocyanic acid compound while a pH of the mixture is kept at not less than 8.0 and not more than 13.5, wherein an amount of the isocyanic acid compound is not less than 0.9 times by mole and not more than 1.1 times by mole relative to an amount of the tert-leucine. According to the present invention, it becomes possible to easily produce an N-carbamoyl-tert-leucine with high efficiency, while the generation of by-products such as a dipeptide-like compound and a urea compound is prevented.

5 Claims, No Drawings

PROCESS FOR PRODUCTION OF N-CARBAMOYL-TERT-LEUCINE

TECHNICAL FIELD

The present invention relates to a process for producing an N-carbamoyl-tert-leucine which is useful as an intermediate for various pharmaceutical products and agrochemicals.

BACKGROUND ART

An N-carbamoyl-tert-leucine, which can be produced by carbamoylizing the amino group of tert-leucine, i.e. 2-amino-3,3-dimethyl butanoic acid, is useful as a synthesis intermediate for various pharmaceutical products and agrochemicals. In particular, it is reported in Patent Document 1 that N-tert-butylcarbamoyl-L-tert-leucine is very useful as a precursor of a hepatitis C virus protease inhibitor.

In general, it has been well-known as a method for synthesizing an N-carbamoyl-amino acid that an amino acid is mixed with an isocyanic acid compound for reaction (Non-patent Document 1 and Patent Document 2).

Non-patent Document 1: "Jikken Kagaku Koza (The course of chemical experiment) 5$^{th}$ edition", MARUZEN Co. Ltd., vol. 14, p. 429
Patent Document 1: JP 2006-528133 T
Patent Document 2: JP 60-155968 A

DISCLOSURE OF THE INVENTION

Problems to be Solved by the Invention

However, as a result of in-depth study by the present inventors, it was found that an N-carbamoyl-tert-leucine cannot be efficiently produced by the above method, since a dipeptide-like compound due to dimerization and a urea compound derived from an isocyanic acid compound are generated as by-products.

The above "a dipeptide-like compound" is a condensation product of an N-carbamoyl-tert-leucine and tert-leucine, and the "a urea compound" is a reaction product of an isocyanic acid compound and an amine compound generated as a by-product by the degradation of an isocyanic acid compound.

Under the above circumstance, the objective of the present invention is to provide a method for producing an N-carbamoyl-tert-leucine with high efficiency, while the generation of by-products such as a dipeptide-like compound and a urea compound is prevented.

Means for Solving the Problems

The present inventors made various investigations to solve the above-mentioned problems; and as a result, found that it becomes possible to easily produce an N-carbamoyl-tert-leucine with high efficiency by controlling the pH during the reaction and the ratio of reagents used for the reaction.

The present invention relates to a process for production of an N-carbamoyl-tert-leucine (2), comprising a step of mixing tert-leucine with an isocyanic acid compound (1) while a pH of the mixture is kept at not less than 8.0 and not more than 13.5, wherein an amount of the isocyanic acid compound is not less than 0.9 times by mole and not more than 1.1 times by mole relative to an amount of the tert-leucine.

Effect of the Invention

By the present invention, it becomes possible to easily produce an N-carbamoyl-tert-leucine with high efficiency, while the generation of by-products such as a dipeptide-like compound and a urea compound is prevented.

BEST MODE FOR CARRYING OUT THE INVENTION

In the present invention, an N-carbamoyl-tert-leucine represented by the general formula (2):

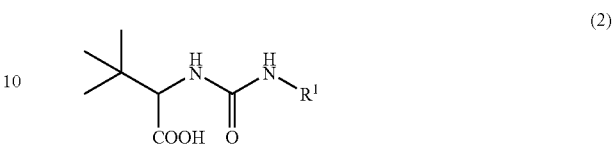

can be produced by reacting tert-leucine with an isocyanic acid compound represented by the general formula (1):

$$R^1-N=C=O \quad (1).$$

$R^1$ in the general formula (2) is derived from an isocyanic acid compound used for the reaction, and is the same as $R^1$ in the general formula (1).

First, the precursor compound used in the present invention and the target compound are explained.

In the isocyanic acid compound represented by the general formula (1):

$$R^1-N=C=O \quad (1)$$

and used in the present invention (hereinafter, the compound is sometimes described as "isocyanic acid compound (1)"), $R^1$ is a hydrogen atom, an optionally substituted alkyl group having 1 to 10 carbon atoms, or an optionally substituted aryl group having 6 to 12 carbon atoms.

The alkyl group having 1 to 10 carbon atoms is not particularly limited, and may be linear, branched, cyclic or non-cyclic. The examples thereof include a methyl group, an ethyl group, a n-propyl group, an i-propyl group, a n-butyl group, an i-butyl group, a t-butyl group, a n-pentyl group, a cyclopentyl group, a n-hexyl group, a cyclohexyl group, a n-heptyl group, a n-octyl group, a n-nonyl group, a n-decyl group, and the like.

The aryl group having 6 to 12 carbon atoms is not particularly limited. The examples thereof include a phenyl group, an indenyl group, a biphenyl group, a naphthyl group, and the like.

Among the above, $R^1$ is preferably an alkyl group having 1 to 10 carbon atoms and an aryl group having 6 carbon atoms, more preferably an alkyl group having 2 to 6 carbon atoms and an aryl group having 6 carbon atoms, more preferably an ethyl group, a n-propyl group, an i-propyl group, a n-butyl group, an i-butyl group, a t-butyl group, and most preferably a t-butyl group.

The substituent for the alkyl group and the aryl group is not particularly limited, and the examples thereof include a halogen atom, a hydroxy group, an amino group, a carboxy group, an ether group, and the like.

The optical purity of tert-leucine used in the present invention is not particularly limited, and a racemic substance or an optically-active substance thereof can be used. In the method of the present invention, when an optically-active substance is used, the target compound can be obtained without racemization.

The commercial product of tert-leucine may be used, and tert-leucine produced by a conventional method may be also used. For example, tert-leucine can be synthesized by the reaction described in JP 10-72419 A and the biological reaction described in JP 9-504304 T. The morphology of tert-leucine to be used is not particularly limited, and both of the crystal thereof and the solution thereof, such as the aqueous solution, can be used.

Next, the conditions of the reaction in the present invention are specifically explained.

A solvent used in the present invention is not particularly limited, and both of water and an organic solvent can be suitably used. The organic solvent is not particularly limited, and the examples thereof include aliphatic hydrocarbon solvents such as pentane, hexane, heptane and octane; aromatic hydrocarbon solvents such as benzene, toluene and xylene; halogenated solvents such as methylene chloride, chlorobenzene, chloroform and 1,1,1-trichloroethane; ether solvents such as tetrahydrofuran, 1,4-dioxane, diethylether, methyl tert-butyl ether and dibutylether; ester solvents such as ethyl acetate, n-propyl acetate, isopropyl acetate, n-butyl acetate and tert-butyl acetate; ketone solvents such as acetone, methy ethyl ketone and methyl isobutyl ketone; alcohol solvents such as methanol, ethanol, propanol and butanol; nitrile solvents such as acetonitrile; amide solvents such as N,N-dimethylformamide, N,N-dimethylacetoamide and N-methylpyrrolidone; other solvents such as dimethylsulfoxide. The organic solvents and water may be singly used, and the two or more solvents are mixed at arbitrary ratio to be used. The order for the mixing is not particularly limited.

Among the examples, in order to achieve a preferable reactivity and a high flowability of the reaction mixture even when a small amount of solvent is used, water and/or a water-miscible solvent are preferable, and water and/or tetrahydrofuran, 1,4-dioxane, acetone, acetone, methanol, ethanol, isopropanol, acetonitrile are more preferable, since the solubility of tert-leucine, which is an amino acid, to water and a water-miscible solvents is high.

The use amount of the solvent is not particularly limited; however, the amount of singly used solvent or the total amount of mixed solvents is preferably not less than 1 time by weight and not more than 50 times by weight, more preferably not less than 2 times by weight and not more than 20 times by weight, relative to tert-leucine, in terms of production efficiency.

A mineral salt may exist as a coexisting material other than an organic solvent. The examples of such a mineral salt which may coexist include sodium chloride, ammonium chloride, potassium chloride, sodium sulfate, ammonium sulfate and ammonium bromide; however, the mineral salt is not limited thereto, and it can be evaluated with a simple experiment whether the mineral salt may coexist or not.

A reaction temperature in the present invention is not particularly limited; however, the present invention can be generally practiced from the solidification point to the boiling point of a solvent, and the temperature is preferably −20° C. to 100° C., and more preferably −10° C. to 50° C. The boiling point of a solvent is generally dependent on pressure, and the reaction can be carried out under any of reduced pressure and increased pressure in addition to ordinary pressure.

The value of pH during the reaction is controlled into the predetermined range described below. If the value of pH during the reaction is low, the time of the reaction tends to be prolonged and a dipeptide-like compound to be dimerized is easily generated. On the other hand, if the value of pH during the reaction is high, it becomes easier that the isocyanic acid compound (1) is degraded and a urea compound which is condensation product of an amine compound generated by the degradation with the isocyanic acid compound (1) is generated as by-products. The present inventors found that the quality and yield of the product become inferior and the production efficiency is decreased, if the pH range of the reaction mixture is not adequately controlled.

The lower limit of the adequate pH range is 8.0, preferably 8.5, more preferably 9.0. The upper limit is 13.5, preferably 13.0. However, the pH may be out of the above range in a short time such that each impurity does not continue to be intermittently generated.

The means for controlling the pH to the above range is not limited. In general, the pH which is decreased with the progress of the reaction may be controlled to the above range using a base; and the pH may be controlled to relatively-high level in the above range at earlier stage of the reaction and regulated in the reaction as need arises as long as the reaction can be completed in the above pH range. In addition, the addition order, addition rate, and addition means, such as continuous addition and intermittent addition, for the reagents is not limited as long as pH is maintained in the range.

The base used in the present invention is not limited as long as the reaction of tert-leucine with the isocyanic acid compound (1) is not inhibited. The examples thereof to be used include hydroxides of alkali metal, such as sodium hydroxide and potassium hydroxide; hydroxides of alkaline-earth metal, such as magnesium hydroxide and calcium hydroxide; carbonates of alkali metal, such as sodium carbonate and potassium carbonate; hydrogencarbonates of alkali metal, such as sodium hydrogencarbonate and potassium hydrogencarbonate; organic bases such as pyridine and triethylamine. Among the examples, inorganic bases are preferable, and hydroxides of alkali metal, carbonates of alkali metal and hydrogencarbonates of alkali metal are more preferable, for the low price and handling property thereof. The bases may be used as a solution such as aqueous solution and also in the solid state.

Next, the quantitative ratio of tert-leucine and the isocyanic acid compound (1).

As mentioned above, if the amount of the isocyanic acid compound (1) is much higher than that of tert-leucine, a lot of a urea compound derived from the degradation of the isocyanic acid compound is generated as by-products, and the yield and quality of the compound (2) are decreased. The use amount of the isocyanic acid compound (1) relative to tert-leucine should be decreased in order to avoid the circumstance; however, the yield is naturally.reduced if the decreased amount is too much. In addition, needless to say, a residual tert-leucine is mixed in the compound (2), to decrease the quality. Therefore, there is an optimum range of the use amount of the isocyanic acid compound (1) in order to optimize a production efficiency. The lower limit thereof is 0.9 times by mole, preferably 0.95 times by mole, relative to tert-leucine. The upper limit thereof is 1.1 times by mole, preferably 1.05 times by mole, relative to tert-leucine.

The N-carbamoyl-tert-leucine represented by the general formula (2) can be produced by the above-mentioned method. The compound is sometimes called. as "the compound (2)". The means for obtaining the compound (2) as the target compound from the reaction mixture is not limited, and a general post-processing method can be carried out. In general, the compound (2) can be obtained by acidifying the solution by adding a general acid such as hydrochloric acid and sulfuric acid, since the compound (2) which is a carboxy compound exists as a salt of the used base in the above pH range. On this occasion, if the target compound is liberated as a solid, the target compound can be obtained as the solid by separation. However, if the target compound is not liberated as a solid or the intended purification efficiency and yield cannot be achieved, extraction operation may be carried out by adding a general organic solvent such as toluene, ethyl acetate, diethylether and hexane.

The organic solvent used for extraction operation is not limited, though the organic solvent should be selected depending on the solubility of the compound (2). The organic solvent may be singly used or two or more solvents are mixed to be used in combination. When the above water or water-miscible solvent which often acts as good solvent is used in combination with the general solvent for extraction, the extraction concentration can be increased in some cases.

The extract may be directly used for crystallization operation; and the extract may be washed by water for removing water-soluble impurities or the target compound may be dissolved into water layer again by alkalifying the mixture for removing impurities, if necessary. When the target compound is dissolved into water again, the target compound can be crystallized or extracted into an organic solvent by acidifying the mixture again.

The target compound can be crystallized by treating thus obtained solution of the target compound with well-known crystallization operation such as cooling crystallization, concentration crystallization and crystallization by adding poor solvent. In addition, crystallization by adding a suitable base to the target compound and then forming a salt may be carried out to obtain crystals. Thus obtained target compound is almost pure; however, the purity thereof may be further increased by a general purification operation such as column chromatography.

EXAMPLES

Hereinafter, the examples of the present invention are described; however, it is not intended that the present invention be limited to the examples.

The quantity of an N-carbamoyl-tert-leucine, the purity, and the quantity of a dipeptide-like compound and a urea compound as by-products were determined by the following HPLC condition 1, and Calculation formulae 1, 2 and 3.

HPLC Condition 1
Column: Water Symmetry C18 (3.5 μm, 150 mm×4.6 mm i.d.)
Column temperature: 35° C.
Detection Device: UV Detection Device (wavelength: 210 nm)
Moving phase: The following time program was adopted. In the table, "Moving phase A" is a 0.1% by weight aqueous phosphoric acid, and "Moving phase B" is acetonitrile.

TABLE 1

The ratio of HPLC Moving phases A and B

| Time (min) | Moving phase A | Moving phase B |
|---|---|---|
| 0 | 95 | 5 |
| 25 | 5 | 95 |
| 30 | 5 | 95 |
| 30.1 | 95 | 5 |
| 45 | STOP | |

Flow speed: 1.0 ml/min

The amount of a dipeptide-like compound(%)=(the value of the area of a dipeptide-like compound)/(the value of the area of an N-carbamoyl-tert-leucine)　　　Calculation formula 1

The amount of a urea compound(%)=(the value of the area of a urea compound)/(the value of the area of an N-carbamoyl-tert-leucine)　　　Calculation formula 2

The purity of an N-carbamoyl-tert-leucine(%)=(the value of the area of an N-carbamoyl-tert-leucine)/(the value of the total area)　　　Calculation formula 3

In the Examples, the enantiomer amount in an N-carbamoyl-tert-leucine was determined by the following HPLC condition 2 and Calculation formula 4.

HPLC Condition 2
Column: CHIRALPAK AS-H manufactured by DAICEL CHEMICAL INDUSTRIES LTD. (250 mm×4.6 mm i.d.)
Column temperature: 30° C.
Detection Device: UV Detection Device (wavelength: 210 nm)
Moving phase: n-hexane/isopropanol=90/10 (v/v)
Flow speed: 1.0 ml/min The enantiomer amount(%)=(the value of the area of enantiomer)/(the value of the area of an N-carbamoyl-tert-leucine)　　　Calculation formula 4

Example 1

The pH of a stirred aqueous solution (1150 g) containing tert-leucine (100 g, 762 mmol) was adjusted to 11.5 using a 48% by weight aqueous sodium hydroxide solution. Thereafter, tert-butyl isocyanate (75.5 g, 762 mmol) was slowly added thereto in an ice bath. The reaction was completed in 6 hours after the addition. The reaction mixture was analyzed with HPLC; as a result, it was found that 172 g of N-tert-butylcarbamoyl-tert-leucine was generated (yield: 98%), and 0.02% of a dipeptide-like compound and 0.07% of N,N'-di(tert-butyl)urea were generated. The pH of the reaction mixture after the reaction was 9.3.

Example 2

The pH of a stirred aqueous solution (1150 g) containing L-tert-leucine (100 g, 762 mmol) was adjusted to 11.5 using a 48% by weight aqueous sodium hydroxide solution. Thereafter, tert-butyl isocyanate (75.5 g, 762 mmol) was slowly added thereto in an ice bath. The reaction was completed in 6 hours after the addition. The reaction mixture was analyzed with HPLC; as a result, it was found that 172 g of an N-tert-butylcarbamoyl-L-tert-leucine was generated (yield: 98%), and 0.02% of a dipeptide-like compound and 0.07% of N,N'-di(tert-butyl)urea were generated. The amount of the enantiomer was below measurable limits, i.e., 0.01%. The pH of the reaction mixture after the reaction was 9.3.

Example 3

A reaction was carried out in the same condition as Example 1 except that the pH at a primacy stage was adjusted to 12.4 using a 48% by weight aqueous sodium hydroxide solution and the use amount of tert-butyl isocyanate was 83.1 g (838 mmol). When the reaction was completed, in other words, 6 hours after the addition of tert-butyl isocyanate, 174 g of N-tert-butylcarbamoyl-tert-leucine was generated (yield: 99%), the pH of the reaction mixture was 8.6, and 0.3% of a dipeptide-like compound and 0.2% of N,N'-di(tert-butyl)urea were generated.

To the obtained aqueous solution, ethyl acetate (1200 g) was added; and the target compound was extracted by adjusting the pH to 3.0 using 35% hydrochloric acid. After the extract was washed with water (200 g), the mixture was concentrated to about 1/5. Thereafter, toluene (700 g) was added to the mixture. The precipitated crystals were separated and dried, to obtain white crystals of N-tert-butylcarbamoyl-tert-leucine (168 g, yield: 96%, purity: 99.9%).

Example 4

The pH of a stirred aqueous solution (20.6 g) containing tert-leucine (2.40 g, 18.3 mmol) was adjusted to 12.5 using a 30% by weight aqueous sodium hydroxide solution. Thereafter, phenyl isocyahate (2.18 g, 18.3 mmol) was slowly added thereto at ambient temperatures. After the mixture was stirred for 3 hours, 4.49 g of an N-phenylcarbamoyl-tert-leucine was generated (yield: 98%), the p1-1 was 10.6, and dipeptide-like compound was not detected and 0.5% of N,N'-diphenylurea were generated.

Comparative Example 1

The pH of a stirred aqueous solution (574 g) containing tert-leucine (66.2 g, 505 mmol) was adjusted to 10.3 using a 48% by weight aqueous sodium hydroxide solution. Thereafter, tert-butyl isocyanate (50.8 g, 512 mmol) was slowly added thereto in an ice bath. After the mixture was stirred for 13 hours, 101 g of an N-tert-butylcarbamoyl-tert-leucine was generated (yield: 87%), the pH was 7.6, and 5.3% of dipeptide-like compound and 0.2% of N,N'-di(tert-butyl)urea were generated.

Thereafter, the pH was anew adjusted to 11.0 using a 48% by weight aqueous sodium hydroxide solution; however, the change of the result was not observed in the vicinity of the pH adjustment.

Comparative Example 2

The pH of a stirred aqueous solution (45.0 g) containing tert-leucine (4.47 g, 34.1 mmol) was adjusted to 10.2 using a 48% by weight aqueous sodium hydroxide solution. Thereafter, tert-butyl isocyanate (4.06 g, 41.0 mmol) was slowly added thereto in an ice bath. When the reaction was completed, 7.15 g of N-tert-butylcarbamoyl-tert-leucine was generated (yield: 91%), the pH was 8.2, and 0.3% of dipeptide-like compound and 5.6% of N,N'-di(tert-butyl)urea were generated.

The invention claimed is:

1. A process for production of an N-carbamoyl-tert-leucine represented by the general formula (2):

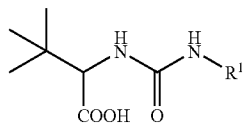

(2)

wherein, $R^1$ is a hydrogen atom, an optionally substituted alkyl group having 1 to 10 carbon atoms, or an optionally substituted aryl group having 6 to 12 carbon atoms,
comprising a step of mixing tert-leucine with an isocyanic acid compound represented by the general formula (1):

 (1)

wherein, $R^1$ is the same as described above,
while a pH of the mixture is kept at a range of not less than 8.0 and less than 13.0,
wherein the amount of the isocyanic acid compound is not less than 0.9 times by mole and not more than 1.1 times by mole relative to the amount of the tert-leucine.

2. The production process according to claim 1, wherein $R^1$ is an alkyl group having 2 to 6 carbon atoms or an aryl group having 6 carbon atoms.

3. The production process according to claim 1, wherein the N-carbamoyl-tert-leucine represented by the general formula (2) is an optically-active substance.

4. The production process according to claim 2, wherein the N-carbamoyl-tert-leucine represented by the general formula (2) is an optically-active substance.

5. The production process according to claim 1, wherein the total amount of a single solvent or a mixed solvent in the reaction mixture is not less than 2 times by weight and not more than 20 times by weight relative to the amount of the tert-leucine.

* * * * *